United States Patent [19] [11] 3,954,962
Prussin [45] May 4, 1976

[54] ORAL HYGIENE PRODUCT

[75] Inventor: Samuel B. Prussin, Los Angeles, Calif.

[73] Assignees: Alan R. Tripp; Samuel Grubstein; Eugene F. Whelan; E. R. Finnis; Samuel Prussin, all of New York, N.Y.

[22] Filed: Apr. 1, 1974

[21] Appl. No.: 456,779

[52] U.S. Cl. .................................. 424/49; 424/54; 424/56
[51] Int. Cl.² .......................................... A61K 7/16
[58] Field of Search ............................. 424/49–58

Primary Examiner—Richard L. Huff
Attorney, Agent, or Firm—Amster & Rothstein

[57] ABSTRACT

An essentially non-aqueous oral hygiene product is disclosed comprising an alcohol base, a combination of viscosity adjusters, e.g., polyvinylpyrrolidone and glycerin; a detergent such as sodium lauryl sulfate; a sweetening agent such as saccharin, and a flavor additive. The combination of viscosity adjusters imparts a suitable viscosity and body to the product to enable it to adhere to a toothbrush and be readily dispersible in water to be used as a mouthwash.

8 Claims, No Drawings

ORAL HYGIENE PRODUCT

This invention relates to an oral hygiene product which is useful as a dentifrice and when added to water is also a mouthwash.

In a combination dentifrice and mouthwash product, many of the properties required of the dentifrice are antagonistic to the properties required for the mouthwash. A dentifrice must have sufficient viscosity and body to be retained by the bristles of the toothbrush. This requirement is antagonistic with the major parameter required of the mouthwash, that is, good dispersibility and solubility in water.

A combination of ingredients has been discovered which satisfies the mutually antagonistic requirements of the dentifrice and the mouthwash. The oral hygiene product of this invention is retained by the bristles of the toothbrush and is readily soluble in water for use as a mouthwash. The product has excellent dispersibility. Because of its low surface and interfacial tensions and ready dispersibility, the product readily penetrates into the dental interstices, fine cracks and fissures of the oral cavity and effectively removes debris from the oral cavity by the mechanisms of emulsification, suspension and floatation. The product has the added advantages of having a good mouth-feel and of not leaving an unpleasant after-taste notwithstanding the fact that large amounts of sodium lauryl sulfate and saccharin are contained therein.

The ideal properties of the dentifrice and mouthwash are achieved by the use of a ternary system comprising an alcohol and two viscosity adjusters, preferably polyvinylpyrrolidone and glycerin. The alcohol used in the system is ethyl alcohol denatured with menthol or the like. The product is essentially non-aqueous, i.e., it contains, as formulated, only that water which is contributed by the raw materials.

The following materials may be used as the first viscosity adjuster: polyvinylpyrrolidone; low molecular weight, partially hydrolyzed, cold water soluble polyvinyl alcohol; methyl cellulose; carboxy vinyl polymers of extremely high molecular weight such as Carbopol 934 and 944; hydroxypropyl cellulose, e.g., the material sold by Hercules Inc. under the name KLUCEL; and block polymer polyols having a molecular weight of from 1000 to 15,500. Other suitable polymeric viscosity builders may be used.

Polyvinylpyrrolidone is the preferred first viscosity adjuster. It helps, to a much greater extent than the other adjusters, to impart a fully rounded, polished flavor and better body and mouthfeel to the product; and there is no hint of the unpleasant fatty alcohol taste in products containing polyvinylpyrrolidone even though large amounts of sodium lauryl sulfate are present. The polyvinylpyrrolidone should have a molecular weight of from about 10,000 to 360,000, preferably from 15,000 to 30,000. According to the Encyclopedia of Chemical Technology, Vol. 21, 2nd Ed., in an article entitled "Polyvinylpyrrolidone", polyvinylpyrrolidone is manufactured in the United States in four viscosity grades, K-15, K-30, K-60 and K-90.

The carboxy vinyl polymers sold as Carbopol 934, etc. have extremely high molecular weights ranging from 1,000,000 to 4,000,000 and are supplied in the acid form. Carbopol 934, for example, has the appearance of a fluffy white powder, a bulk density of 13 pounds per cubic foot, a specific gravity of 1.41, and a moisture content as shipped of 2% maximum. B. F. Goodrich is the supplier of these Carbopol products.

The block polyols are made by adding propylene oxide to the two hydroxyl groups of a propylene glycol nucleus. These materials are sold as Pluronic Polyols by Wyandotte Chemical Corporation.

Certain non-ionic polymers of ethylene oxide may also be used as the first viscosity adjuster. These materials are sold by Union Carbide as Polyox resins. Their molecular weights range from several hundred thousand to five million and above. Typical properties of the Polyox resins are melting points of about 65°C, specific gravities of 1.21 grams per cubic centimeters, bulk densities of 20 pounds per cubic foot, moisture contents as supplied less than 1%, ash contents about 0.5% and heats of fusion being about 33 calories per gram.

These are various commercially available products which can be used as the second viscosity adjuster. For example, it may be a polyol such as glycerin, propylene glycol, 1,3 butylene glycol, sorbitol, pantothenyl alcohol, polyethylene glycols ranging in average molecular weights from 150–2000, and ethylene oxide condensates of between 20 and 1,000 ethylene oxide groups of fatty acids with 12 to 18 carbon atom.

The amount of alcohol used in the product will vary depending upon the number and amount of other ingredients which are added to the ternary system. In general, however, the alcohol should constitute from about 30–44% by weight of the total oral hygiene product, preferably from 30–36%.

The amount of the viscosity adjusters and the relative proportions thereof will vary somewhat depending on the selection of the adjuster and the amount and number of other ingredients added. The viscosity of the system is particularly sensitive to the concentration of the flavor oils. In general, however, the first adjuster, e.g., polyvinylpyrrolidone having a molecular weight of 30,000, should be present in an amount ranging from 20 – 35% by weight of the total product, preferably from about 22 – 29%; and the second viscosity adjuster, e.g., glycerin, should be present in an amount ranging from 28% down to about 3%, preferably from 28% down to about 12%.

The amount and relative proportions of the viscosity adjusters should be selected so that the resulting oral hygiene product will have a viscosity and body sufficient to adhere to the bristles of a toothbrush. In other words, the oral hygiene product should have a viscosity within the range of from about 360 to 3800 centipoise, preferably from 750 to 2500 centipoise, at the temperature at which it will be used.

The detergents which can be effectively used in this oral hygiene product include sodium lauryl sulfate, sodium lauryl sulfoacetate, sodium lauroyl sarcosinate and the block polymer polyols described above.

The preferred detergent is sodium lauryl sulfate which typically has the following specification: 98.5 – 99.5% actives, 0.2 – 0.5% free fatty alcohol, 0.2 –0.1% sodium chloride, and 0.05 – 0.1% sodium sulfate. The detergent can be included in amounts of to about 7.5 weight percent of the total oral hygiene product. Generally, it should be present in the range of from 0.25 – 7.5%, preferably from 5 – 7.5% by weight of the total oral hygiene product.

In a preferred embodiment, saccharin, cyclamates or a combination thereof are added to the composition in an amount in the range of from about 1 to 3% by weight of a total oral hygiene product.

A wide variety of flavor compositions can be compounded from an extensive number of commercially available ingredients including cinnamon oil, menthol, methyl salicylate, oil of spearmint, peppermint oil, oil of eucalyptus, oil of cloves, and various imitation flavor compositions made from synthetics alone or in combination with natural oils. The flavor additives should generally be present in amounts ranging from 2.0 to about 12% by weight of the oral hygiene product.

Various other additives may be included. Thus, for example, sodium lauroyl sarcosinate may be added as an anti-enzyme or anti-cavity agent; fluoride may be added in the form of stannous fluoride or sodium fluoride and polishing agents such as sodium chloride, sodium bicarbonate, calcium carbonate, dicalcium phosphate, and insoluble sodium metaphosphate may also be added.

The following is a description of the oral hygiene product containing the preferred ingredients in the acceptable and preferred ranges:

| Preferred Ingredient | Acceptable Range (% by weight of total product) | Preferred Range (% by weight of total product) |
|---|---|---|
| ethyl alcohol denatured with menthol | 30.00 – 44.00 | 30.00 – 39.00 |
| polyvinylpyrrolidone molecular weight 30,000 | 22.00 – 33.00 | 22.00 – 29.00 |
| sodium lauryl sulfate | 0.25 – 7.50 | 5.00 – 7.30 |
| glycerin, 95% (USP) | 28.00 – 3.00 | 28.00 – 12.00 |
| saccharin | 1.50 – 3.00 | 2.00 – 2.75 |
| oil of cinnamon/oil of peppermint in a ratio of one to one | 2.50 – 10.00 | 5.00 – 10.00 |

The amounts of sodium lauryl sulfate, saccharin and flavor additive will vary depending on the desired foam, flavor intensity, and sweetness desired as well as economic factors.

The oral hygiene products are easily formulated. The products may be made simply by dissolving the polymeric viscosity adjuster in alcohol and adding, with suitable mixing, the second viscosity adjuster, e.g., glycerin, in which the detergent and sweetener have been thoroughly dispersed. Finally, the flavor is added and dissolved to complete the formulation.

The oral hygiene products of this invention are illustrated by the following examples:

EXAMPLE I

A combination dentifrice and mouthwash is formulated by dissolving 25.75 pounds of polyvinylpyrrolidone (PVP K-30) having a molecular weight of 30,000 into 33.71 pounds of ethyl alcohol denatured with menthol, USP. 7.29 pounds of sodium lauryl sulfate, and 2.55 pounds of saccharin, USP, are throughly dispersed in 20.60 pounds of glycerin, USP. This material is then combined with the alcohol solution and 10.40 pounds of cinnamon oil, USP, is added with sufficient mixing to obtain an essentially homogeneous consistency.

This oral hygiene product adheres to a toothbrush and is readily convertible into a mouthwash by mixing a few drops with water. The product effectively removes debris from the oral cavity, has good mouth-feel, and leaves no bitter after-taste even though relatively large amounts of saccharin and sodium lauryl sulfate are used. The product is readily soluble in water notwithstanding its high viscosity and the pressure of a large concentration of flavor oil.

The product is a clear amber viscous liquid having a specific gravity at 25°C of 1.093. It is preferably used at a temperature of from 55°F to 120°F. It is thick and turbid at 50°F, but useable.

The viscosity and physical appearance of the product at various temperatures is described in the following table:

| Temperature °C | Viscosity Centipoise | Physical Appearance |
|---|---|---|
| 4.0 | 7700 | Extremely thick, turbid barely useable |
| 7.5 | 3800 | Very thick, useable |
| 10.0 | 2500 | Thick, useable |
| 15.0 | 1400 | Clear thick fluid |
| 20.0 | 1050 | Clear thick fluid |
| 25.0 | 750 | Clear thick fluid |
| 30.0 | 600 | Clear fluid - becoming thinner with increasing temperature |
| 35.0 | 480 | Same as above |
| 40.0 | 360 | Same as above |

EXAMPLE II

A combination dentifrice and mouthwash is prepared as follows: 1.15 pounds of a hydroxypropyl cellulose (KLUCEL HAP, HERCULES INCORPORATED) is dissolved in 58.91 pounds of ethyl alcohol. 3 pounds of saccharin, USP, and 4 pounds of sodium lauryl sulfoacetate are thoroughly dispersed in 25.44 pounds of glycerin, USP. This phase is combined with the alcohol solution and 7.5 pounds of peppermint oil, USP, is added with sufficient stirring to obtain a substantially homogeneous product.

This product adheres to the bristles of a toothbrush for use as a dentifrice and disperses in water for use as a mouthwash.

EXAMPLE III 5 pounds of a non-ionic polymer of ethylene oxide (Polyox WSRN-80) is dissolved in 54.5 pounds of the ethyl alochol and 2 pounds of water. The second viscosity adjuster comprising 7.5 pounds of propylene glycol, USP, and 7.5 pounds of glycerin, USP, is combined with a combination of detergents comprising 2.5 pounds of sodium lauroyl sarcosinate and 3.5 pounds of sodium lauryl sulfate, 2.5 pounds of saccharin, USP, 3 pounds of menthol, USP, and 12 pounds of methyl salicylate. This mixture is then added to the alcohol solution with sufficient stirring to obtain a substantially homogeneous product.

This product adheres to a toothbrush and is readily dissolvable in water for use as a mouthwash.

The products have been described with particularlity. Various additions and some substitutions can be made without departing from the scope of the invention.

What is claimed is:

1. An essentially non-aqueous oral hygiene product comprising (a) at least 30% by weight of total product of a suitable alcohol; (b) a first viscosity adjuster selected from the group consisting of polyvinylpyrrolidone having a molecular weight of 10,000 to 360,000, a low molecular weight, partially hydrolyzed, cold water soluble, methyl cellulose, hydroxy propyl cellulose, a high molecular weight carboxy vinyl polymer, non-ionic polymers of ethylene oxide, and a block polymer polyol having a molecular weight of from 1,000 to 15,500; (c) a second viscosity adjuster selected from the group consisting of glycerin, propylene glycol, 1,3 butylene glycol, sorbitol, pantothenyl alcohol, polyethylene glycols ranging in average molecular weights from 150 – 2000, and ethylene oxide condensates of between 20 and 1,000 ethylene oxide groups of fatty acids with 12 to 18 carbon atom; and (d) a suitable detergent; said first and second viscosity adjusters being present in amounts and relative proportions sufficient to give said product a viscosity and body sufficient to hold the desired amount of detergent and other ingredients which may be added and to adhere to a toothbrush; whereby the oral hygiene product is a dentifrice capable of effective debris removal and is readily convertible to a mouthwash by the addition of water.

2. A non-aqueous oral hygiene product according to Claim 1 wherein said first viscosity adjuster is polyvinylpyrrolidone having a molecular weight of 10,000 to 360,000 and said second adjuster is glycerin.

3. An oral hygiene product according to Claim 1 wherein said product has a viscosity of from 360 to 3800 centipoise at the proposed temperature of use.

4. An oral hygiene product according to claim 1 wherein said product has a viscosity within the range of from 750 to 2500 centipoise at the proposed temperature of use.

5. A non-aqueous oral hygiene product comprising (a) from 30 – 45% by weight of the total product of a suitable alcohol; (b) polyvinylpyrrolidone having a molecular weight of 10,000 to 360,000; (c) glycerin; said polyvinylpyrrolidone and glycerin being present in amounts and relative proportions sufficient to impart to said product a viscosity within the range of 360 – 3800 centipoise at the proposed temperature of use; (d) an effective amount of a detergent; and (e) an amount sufficient to impart the desired flavor to the product of a suitable flavor additive.

6. An oral hygiene product according to Claim 5 wherein said alcohol is a denatured ethyl alcohol and said detergent is selected from the group consisting of sodium lauryl sulfate, sodium lauryl sulfoacetate and sodium lauroyl sarcosinate.

7. An essentially non-aqueous oral hygiene product comprising (a) from 30 – 45% of a suitable alcohol; (b) 22 – 33% polyvinylpyrrolidone having a molecular weight of 10,000 to 360,000; (c) from 2.5 – 8% of a detergent; (d) from 28 – 3% glycerin; (e) from 1 – 3% saccharin; and (f) from 2.5 – 12% of a suitable flavor additive.

8. An essentially non-aqueous oral hygiene product consisting essentially of (a) from 30 – 39% denatured ethyl alcohol; (b) from 22 – 29% polyvinylpyrrolidone having a molecular weight of 10,000 to 360,000; (c) from 28 – 13% glycerin; (d) from 7 – 7.5% sodium lauryl sulfate; (e) from 2– 3% saccharin; and (f) from 9 – 11% flavor additive.

* * * * *